US007985890B2

(12) United States Patent
Basu et al.

(10) Patent No.: US 7,985,890 B2
(45) Date of Patent: Jul. 26, 2011

(54) TRANSGENIC SWEET SORGHUM WITH ALTERED LIGNIN COMPOSITION AND PROCESS OF PREPARATION THEREOF

(75) Inventors: Asitava Basu, Kharagpur (IN); Mrinal Kumar Maiti, Kharagpur (IN); Satarupa Kar, Kharagpur (IN); Soumitra Kumar Sen, Kharagpur (IN); Banibrata Pandey, Hyderabad (IN)

(73) Assignee: Nagarjuna Energy Private Limited, Hyderabad (IN)

( * ) Notice: Subject to any disclaimer, the term of this patent is extended or adjusted under 35 U.S.C. 154(b) by 0 days.

(21) Appl. No.: 12/545,699

(22) Filed: Aug. 21, 2009

(65) Prior Publication Data

US 2010/0058496 A1 Mar. 4, 2010

Related U.S. Application Data

(63) Continuation of application No. PCT/IB2008/000380, filed on Feb. 20, 2008.

(51) Int. Cl.
*C12N 15/82* (2006.01)
*C12N 15/63* (2006.01)
*C12N 15/29* (2006.01)
*C07H 21/04* (2006.01)

(52) U.S. Cl. ..... 800/286; 800/285; 800/290; 435/320.1; 435/468; 536/23.1; 536/23.6; 536/24.5

(58) Field of Classification Search .................. None
See application file for complete search history.

(56) References Cited

U.S. PATENT DOCUMENTS

| 6,465,229 | B2 | 10/2002 | Cahoon et al. | |
|---|---|---|---|---|
| 2004/0049802 | A1* | 3/2004 | Dixon et al. | 800/278 |
| 2007/0271633 | A9* | 11/2007 | Kovalic et al. | 800/284 |

OTHER PUBLICATIONS

Database EMBL [Online] Jan. 18, 2004, "Corchorus capsularis caffeoyl-CoA-O-methyltransferase mRNA, complete cds."
Database EMBL [Online] Aug. 9, 2005, "4018005B06.2ELx1 4018—RescueMu Grid X Zea mays genomic, genomic survey sequence."
Zhong R et al: "Dual Methylation Pathway in Lignin Biosynthesis" Plant Cell, American Society of Plant Physiologist, Rockville, MD, US, vol. 10, Dec. 1, 1998, pp. 2033-2045.
Dianjing G et al: "Downregulation of Caffeic Acid 3-0-Methyltransferase and Caffeoyl 3-0-Methyltransferase in Transgenic Alfalfa: Impacts on Lignin Structure and Implications for the Biosynthesis of G and S Lignin" Plant Cell, American Society of Plant Physiologists, Rockville, MD, US, vol. 13, Jan. 1, 2001, pp. 73-88.
Marita J M et al: "Structural and compositional modifications in lignin of transgenic alfalfa down-regulated in caffeic acid 3-0-methyltransferase and caffeoyl coenzyme A 3-0-methyltransferase" Phytochemistry, Pergamon Press, B, vol. 62, No. 1, Jan. 1, 2003, pp. 53-65.
Chen Fang et al: "Multi-site genetic modulation of monolignol biosynthesis suggests new routes for formation of syringyl lignin and wall-bound ferulic acid in alfalfa (*Medicago sativa* L.)" Plant Journal, Blackwell Scientific Publications, Oxford, GB, vol. 48, No. 1, Oct. 1, 2006, pp. 113-124.
Martz Francoise et al: "cDNA cloning, substrate specificity and expression study of tobacco caffeoyl-CoA 3-0-methyltransferase, a lignin biosynthesis enzyme" Plant Molecular Biology, vol. 36, No. 3, Feb. 1998, pp. 427-437.
Anterola A M et al: "Trends in lignin modification: a comprehensive analysis of the effects of genetic manipulations/mutations on lignification and vascular integrity" Phytochemistry, Pergamon Press, GB, vol. 61, No. 3, Oct. 1, 2002, pp. 221-294.
Boudet A M et al: "Ligin Genetic Engineering" Molecular Breeding: New Strategies in Plant Improvement, Kluwer Academic Publishers, NL, vol. 2, Jan. 1, 1996, pp. 25-39.
Bout S et al: "A candidate-gene approach to clone the sorghum Brown midrib gene encoding caffeic acid 0-methyltransferase." MGG Molecular Genetics and Genomics, vol. 269, No. 2, May 2003, pp. 205-214.
Database EMBL [Online] Jan. 3, 2002, "Sorghum bicolor 0-methyltransferase mRNA, complete cds."

* cited by examiner

*Primary Examiner* — Brent Page
(74) *Attorney, Agent, or Firm* — Arent Fox LLP

(57) ABSTRACT

The present invention provides a sweet sorghum plant characterized by altered lignin content and/or altered lignin composition compared to a wild plant and this is achieved by manipulating the expression of caffeoylCoA-O-methyltransferae (CCoAOMT) in particular and optionally caffeic acid-O-methyltranferase (COMT) in sweet sorghum by incorporation of a construct comprising an isolated DNA sequence represented by SEQ ID NO 2 and optionally SEQ ID NO 1.

19 Claims, 7 Drawing Sheets

TRANSGENIC SWEET SORGHUM WITH ALTERED LIGNIN COMPOSITION AND PROCESS OF PREPARATION THEREOF

RELATED APPLICATION DATA

This application is a continuation under 35 U.S.C. §120 of International Patent Application No. PCT/IB2008/000380 filed on Feb. 20, 2008, which claims priority to Indian Patent Application No. 1481/CHE/2006 filed on Feb. 21, 2007. The disclosures of both of these priority applications are incorporated herein by reference in their entirety.

BACKGROUND OF THE INVENTION

Sweet sorghum, *Sorghum bicolor* (L.) Moench is the only crop that provides grain and stem that may be used for the production of alcohol, sugar, syrup, fuel etc. But the major problem with this plant is the presence of lignin in cell wall that adversely affects the process of extraction of beneficial materials. Alteration of lignin content is likely to improve the quality of the plant. All conventional breeding programs undertaken to generate cultivars with reduced lignin content met with limited success. Thus, possibility to develop cultivars with altered lignin content through genetic engineering figured as a distinct possibility.

Lignin is considered to be dehydrogenatively polymerized from the monolignols p-coumaryl alcohol, coniferyl alcohol, and sinapyl alcohol. These monolignols are synthesized through the phenylpropanoid pathway. Structurally these monolignols differ only by the methoxy group at the 3C and 5C positions of the aromatic ring. Varying proportion of the monolignols determine the type of lignin. Variation/heterogeneity in lignin molecules depend on the amount of a particular component: when p-coumaryl alcohol is present in higher amount over other components, it is called hydroxyphenyl (H) lignin; when coniferyl alcohol is present in higher amount over other, it is called guaiacyl lignin (G). Similarly, if the content of sinapyl alcohol exceeds the other components, then it is called syringyl lignin (S). G lignin offers more resistance than S during enzymatic degradation. G lignins are more condensed due to more numbers of intermolecular linkages, thereby showing more resistance. It was observed that lignin levels increase with progressive maturity in stems of forage crops, including legumes such as alfalfa (Jung et al., 1997) and in grasses such as tall fescue (Buxton and Redfearn, 1997). Moreover, the lignin composition changes with advanced maturity toward a progressively higher S/G ratio (Buxton and Russell, 1988).

Several approaches have been taken to decrease lignin content and to increase S/G ratio. However, the results have found to be contradictory, possibly due to lack of understanding of lignin biosynthetic pathway and due to inappropriate suitable approaches for down regulation of the lignin biosynthetic enzyme activity including choice of transgene, promoter used, construction of antisense cassettes and above all, selection of transformants. Regulation of early steps enzymes like phenylalanine ammonia lyase, cinnamate 4-hydroxylase, 4-hydroxycinnamate CoA ligase reduced lignin content. However, it leads to pleiotropic effects including altered leaf shape, localised fluorescent lesion, stunted growth, reduced pollen activity, altered flower morphology and pigmentation, reduced level of soluble phenylpropanoids, decrease in S/G ratio etc (Elkind et al, 1990; Bate et al, 1994; Sewalt et al, 1997). Similar effects by other workers to alter or modify the S/G ratio have resulted in phenotypically defective plants. It was demonstrated that down regulation of caffeic acid O-methyltransferase activity could result dramatic decrease in syringyl lignin biosynthesis but with little effect on the synthesis of guaiacyl lignin, which is undesirable as the latter are more resistant to chemical degradation. In this background the present invention provides a novel transgenic sweet sorghum plant having modified lignin content in cell walls using a different approach in construction of the antisense gene cassettes.

DETAILED DESCRIPTION OF THE PRESENT INVENTION

Figure 1:
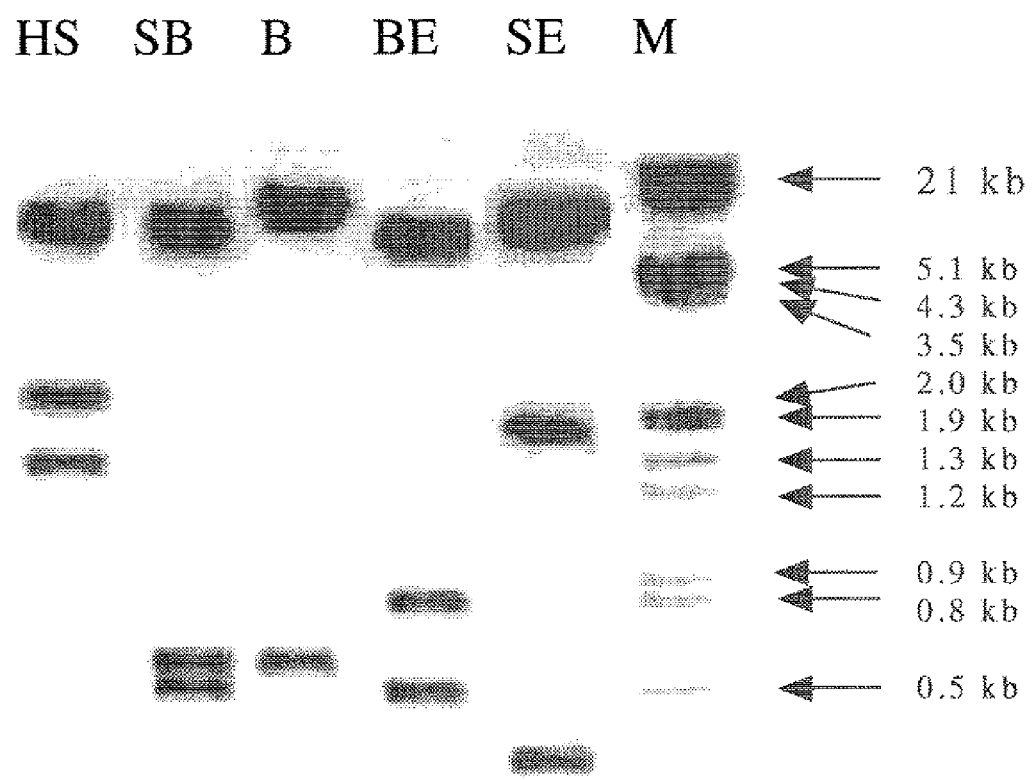
FIG. 1: Restriction analysis of antisense cassettes of CCoAOMT gene for plant transformation
H: Hind III, S: Sacl, B: BamHI, E: EcoRI and M: Lambda DNA digested with HindIII/EcoRI

After extensive experimentation, the Applicant found that lignin composition is influenced by CCoAOMT in particular and COMT in general when manipulated has a direct effect on lignin composition in sweet sorghum plant.

Accordingly, the present invention provides a sweet sorghum plant characterized by altered lignin content and/or altered lignin composition compared to a wild plant and this is achieved by manipulating the expression of caffeic acid-O-methyltranferase (COMT) and caffeoylCoA-O-methyltransferae (CCoAOMT) in sweet sorghum by incorporation of a construct comprising an isolated DNA sequence encoding for caffeoylCoA-O-methyltransferae (CCoAOMT) and represented by SEQ ID NO 2.

In one of the preferred aspects, the sweet sorghum exhibits altered activity of a caffeoyl-CoA O-methyltransferase enzyme. Optionally, the plant additionally exhibits altered activity of a caffeic acid O-methyltransferase enzyme compared to the caffeic acid O-methyltransferase enzyme activity of a wild plant.

Accordingly, a preferred plant of the invention contains at least one exogenous nucleic acid comprising a nucleotide sequence that is "antisense to" at least a portion of a caffeoyl-CoA O-methyltransferase gene such that when the exogenous nucleic acid is transcribed, the activity of the endogenous caffeoyl-CoA O-methyltransferase enzyme is inhibited.

The plant of the invention comprises at least two exogenous nucleic acids, a first comprising a nucleotide sequence that is antisense to at least a portion of a caffeoyl-CoA O-methyltransferase gene and a second comprising a nucleotide sequence that is antisense to at least a portion of a caffeic acid O-methyltransferase gene. The aforesaid construct comprising a first and second exogenous nucleic acid when present regulates the activities of both an endogenous Caffeoyl-CoA-O-methyltransferase enzyme and an endogenous caffeic acid O-methyltransferase enzyme. The exogenous nucleic acids may be present in the plant as part of the same nucleic acid molecule (for example, as when they are present on the same vector); or they may exist as separate molecules (for example, as when they are present on different vectors).

Also provided herewith a process of producing a transgenic plant having altered lignin content. Plants are genetically modified to reduce the activity of one or more enzymes involved in lignin synthesis. In one of the embodiments, the present invention discloses a process for producing a genetically engineered plant that includes transfecting a plant cell with at least one exogenous nucleic acid associated with reduced activity in the plant of at least one biosynthetic enzyme involved in lignin biosynthesis, followed by growing the transfected plant cell into the genetically engineered plant having reduced lignin content compared to the lignin content of a comparable wild plant.

In the present invention the desired enzyme is CCoAOMT and the exogenous nucleic acid includes a nucleotide sequence that is "antisense" to at least a portion of a CCoAOMT gene. Optionally, the plant cell can be additionally transfected with a second exogenous nucleic acid, for example one that is "antisense" to at least a portion of a COMT gene. The transfected plant cell is then grown into a transgenic plant characterized by altered lignin content and/or altered lignin composition compared to a wild plant. The transfected plant cell is then grown into the genetically engineered plant having altered lignin composition.

The exogenous nucleic acids are incorporated into the plant cell by known method such as by means of expression vector. Plant cells containing two or more different antisense nucleic acids can be made by transfecting the plant cell with a single vector that encodes all the desired antisense molecules, or by a plurality of vectors, each encoding one or more antisense nucleic acids. Multiple copies of a single antisense nucleic acid can, but need not be included on a single vector. Preferably, each copy of an antisense nucleic acid is operably linked to its own promoter and terminator.

The CCoAOMT genes (or the gene units) exist in the form which corresponds to the cDNA ("copy" DNA) which is obtainable via mRNA with the aid of reverse transcriptase/polymerase. The CCoAOMT genes can also be present in partially or completely synthetic form. By synthetic genes there are also understood those which are formed by newly joining of parts of natural genes.

Expression Cassettes:

The expression cassette will comprise a selectable marker gene for the selection of transformed cells. Selectable marker genes are utilized for the selection of transformed cells or tissues. Selectable marker genes include genes encoding antibiotic resistance hygromycin phosphotransferase (hptll).

The expression cassettes may contain one or more than one gene or nucleic acid sequence to be transferred and expressed in the transformed plant. Thus, each nucleic acid sequence will be operatively linked to 5' and 3' regulatory sequences. Alternatively, multiple expression cassettes may be provided.

Compositions and methods for the efficient transformation of sorghum for lignin reduction in sweet sorghum (*Sorghum bicolor*) are provided. The transformed sorghum plants are characterized by containing transferred nucleic acid such as a transferred gene or genes of interest flanked by at least one T-DNA border inserted within the genome of the sorghum plants. The plants thus produced are normal in morphology and fertile also.

The enzyme caffeoyl-CoA 3-O-methyltransferase, called CCoAOMT below, catalyses the methylation of caffeoyl-CoA in a biosynthesis route, leads from trans-4-coumaroyl-CoA to trans-feruloyl-CoA. By CCoAOMT genes, there are to be understood any nucleic acid (DNA) which, after its transcription into RNA and translation into protein, causes the formation of an enzyme which has the properties of a CCoAOMT, this nucleic acid being isolated from its natural environment or integrated into a vector or contained as "foreign" DNA or as "additional" DNA in a prokaryotic or eukaryotic DNA. By CCoAOMT genes there are also to be understood those CCoAOMT genes which contain, at their start and/or end, additional DNA sequences which do not or do not substantially impede the function of the genes. These DNA sequences, which are also called "gene units", are formed, for example, by excision with restriction enzymes, since no cleavage sites are available for customary restriction enzymes exactly at the start and at the end of the gene. The CCoAOMT genes or the gene units can also carry at their ends DNA sequences which are appropriate for their handling (for example "linkers").

The methods of the invention are useful for transforming sorghum plant cells. Such cells can be originated from immature embryonic tissue and shoot apical meristem tissue having the potentiality for callus formation. Alternatively, the callus can be originated from anthers, microspores, mature embryos, and in principal from any other tissue of sorghum capable of forming callus and/or secondary embryos. A useful tissue for producing regenerative callus is the shoot apical meristem cut from the germinated seed. Seeds surface sterilized with Tween 20 (5 min) and 0.2% mercuric chloride (7 min) were washed with sterile distilled water. Then seeds were incubated on sterile filter paper soaked with sterile distilled water in petriplates and kept in dark for 3 days for shoot tip generation prior to inoculation with *Agrobacterium*.

Generation of Antisense Cassettes and Transformation Thereof in *Agrobacterium*:

The steps involved in present case for generating antisense cassettes of both the cDNA of caffeic acid-O-methyltransferase (COMT) and caffeoyl-CoA-O -methyltransferae (CCoAOMT) and their introduction into plant cells include:
1) Isolation of mRNA from stem tissue of sorghum plant;
2) Preparation of cDNA from the mRNA;
3) Isolation of desired cDNA;
4) Characterization of the cDNA by sequencing;
5) Construction of gene cassettes by joining the gene fragment in sense and antisense orientation using linker for generation of double stranded RNA;
6) Construction of expression cassettes by placing sense-antisense gene cassettes under a promoter for expression of the respective transcripts;
7) Transformation of the cassettes in *Agrobacterium tumefaciens;*
8) *Agrobacterium tumefaciens* carrying respective gene cassettes was transformed into the suitable explant of sorghum; and
9) Selection of the putative transformants.

The recombinant technology used herein involves standard molecular biological techniques that are well known in art and are described in standard references such as Sambrook et al (1989). Generally, enzymatic reaction involving DNA ligation, DNA polymerase, restriction endo-nucleases and the like are performed according to manufacturer's instruction.

The present invention involves double-stranded RNA-mediated gene interference or convergent hairpin (CV hairpin) RNA approach. The utility of double-stranded RNA (dsRNA)-mediated gene interference has been demonstrated in a variety of organisms, including plants. The advantages of double stranded RNA molecules over single stranded RNA are:

The double-stranded RNA triggers the natural RNaseH dependent degradation of a homologous mRNA.

The resultant double-stranded siRNA molecules form 3'-overhangs that specifically inhibit gene expression.

The double-stranded siRNA possesses unexpectedly high efficacy and stability. It has been demonstrated that less number of dsRNA molecule can produce specific inhibition to abundantly transcribed target which is not possible in case of ssRNA (Montogomery and Fire, 1998).

Preparation of cDNA:

cDNA was prepared from mRNA of sweet sorghum stem by reverse transcription. A primer is annealed to the mRNA providing a free 3' end that can be used for extension by the enzyme reverse transcriptase. The enzyme engages in the usual 5' to 3' elongation, as directed by complementary base pairing with the mRNA template to form a hybrid molecule, consisting of a template RNA strand base paired with the complementary cDNA strand. After degradation of the original mRNA, a DNA polymerase was used to synthesize the complementary DNA strand to convert the single stranded cDNA into a duplex cDNA. Desired complete cDNA was isolated using PCR (Polymerase Chain reaction) with degenerated primers designed from conserved amino acid sequence of the gene from heterologous plant system followed by 5' and 3' RACE (Rapid Amplification of cDNA Ends). After DNA amplification, the double strand DNA was inserted into pUC18 vector for propagation in *E. coli*. Putative recombinant clones were selected by blue-white screening. Identification and characterization of the clones harbouring desired cDNA was performed by sequencing followed by computer analysis.

Generation of sense-antisense construct was made by joining the suitable region of the desired cDNA fragment in sense and antisense orientation through linker. This construct was introduced into an expression vector for transformation of sorghum plants to inhibit the endogenous COMT/CCoAOMT genes. The vector will preferably contain a prokaryotic origin of replication having a broad host range. A selectable marker should also be included to allow selection of bacterial cells bearing the desired construct. Suitable prokaryotic selectable markers include resistance to antibiotics such as kanamycin.

Other DNA sequences encoding additional functions may also be present in the vector, as is known in the art. For instance, in the case of *Agrobacterium* transformations, T-DNA sequences will also be included for subsequent transfer to plant chromosomes.

For expression in plant, a binary vector was used in which gene of interest can be introduced. The recombinant expression cassettes will contain in addition to desired sequences, a plant promoter region, a transcription initiation site and a transcription terminator sequence, Unique restriction enzyme site at the 5' and 3' ends of the cassettes are typically included to allow for easy insertion into a preexisting vector. Sequences controlling eukaryotic gene expression are well known in the art.

Preparation of Promoter for the Present Invention:

Transcription of DNA into mRNA is regulated by a region of DNA referred to as the promoter. The promoter region contains sequence of bases that signals RNA polymerase to associate with the DNA, and to initiate the transcription of mRNA using one of the DNA strands as a template to make a corresponding complementary strand of RNA. Since the 5' region of the RNA strand is complementary to the 3' region, it will generate a double-stranded RNA, which subsequently degraded using machinery responsible for the production short interfering RNA (RNAi). Promoter sequence include the TATA box consensus sequence (TATAAT), which is usually 20-30 base pair (bp) upstream (by convention −30 to −20 bp relative to the transcription start site) of the transcription start site. The TATA box is the only upstream promoter element that has a relatively fixed location with respect to the start point.

The CAAT box consensus sequence is centered at −75, but function at distances that vary considerably from the start point and in either orientation.

Another common promoter element is the GC box at −90 which contains consensus sequence GGGCGG. It may occur in multiple copies and in either orientation.

Other sequence conferring maximum efficiency may also be found in the promoter region. In promoter and structural gene combinations, the promoter is preferably in positioned about the same distance from the heterologous transcription start site as it is from the transcription start site in its natural setting.

The particular promoter used in the expression cassettes is not critical to the invention. Any of the promoters which direct transcription in plant cells is suitable. The promoter can be either constitutive or inducible.

The maize ubiquitin promoter used in the present investigation has been shown to be highly active and constitutively expressed in most tissues. It contains the first intron of the maize ubiquitin gene for selective expression in plants. The promoter was cloned in the vector at HindIII/BamHI site under which the antisense construct of COMT/CCoAOMT was placed. A selectable marker gene, hygromycin phosphotransferase, under 2×35S promoter was included to allow selection of plant cells bearing the desired construct.

Analysis of the Gene Constructs:

A) Restriction Analysis of Antisense Cassettes of COMT Gene for Plant Transformation For restriction analysis, the recombinant DNA was isolated from *Agrobacterium* clones. The method of recombinant DNA isolation is as follows: *Agrobacterium* colonies harboring recombinant plasmid was inoculated in 5 ml of YEP media (Yeast extract 10 g/l, Peptone 10 g/l and Sodium Chloride 5 g/l) and incubated for 36 hrs at 28° C. The collected cells were suspended with Solution I (Glucose 9 g/l, Tris 3 g/l and EDTA 3.72 g/l) and treated with lysozyme (4 mg/ml) at 37° C. for 30 mins. Then Solution II (1% Sodium Dodecyl Sulfate and 0.2N NaOH) was added to it. After 30 mins of incubation at room temperature, Solution III (Potassium acetate 294.4 g/l) was added and kept in ice for 15 mins. The mixture was centrifuged. The collected supernatant was treated with phenol-chloroform and chloroform-isoamyl alcohol sequentially. The plasmid DNA was precipitated out by adding $1/10^{th}$ volume of sodium acetate and double volume of chilled ethanol, kept at −20° C. for 30 mins and centrifuged at 10000 rpm for 10 mins. The pellet was dried and dissolved in TE (1M TRIS and 0.5M EDTA).

The DNA was analysed by restriction digestion with enzymes used for generating the recombinant cassettes and the digested fragments were checked with molecular size marker (FIG. 1).

Figure 2:
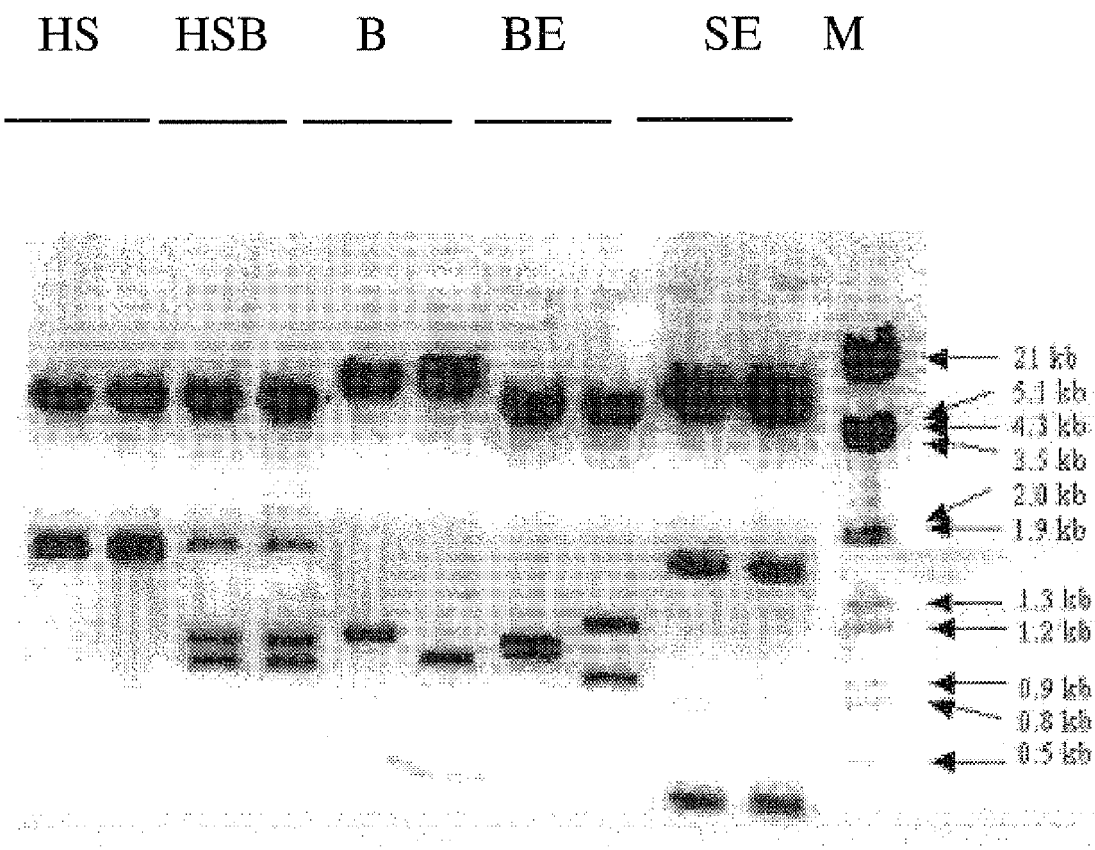
FIG. 2: Restriction analysis of antisense cassettes of COMT gene for plant transformation
H: Hind III, S: Sacl, B: BamHI, E: EcoRI and M: Lambda DNA digested with HindIII/EcoRI
Figure 3:
FIG. 3: Photograph of transgenic plant
Figure 4:
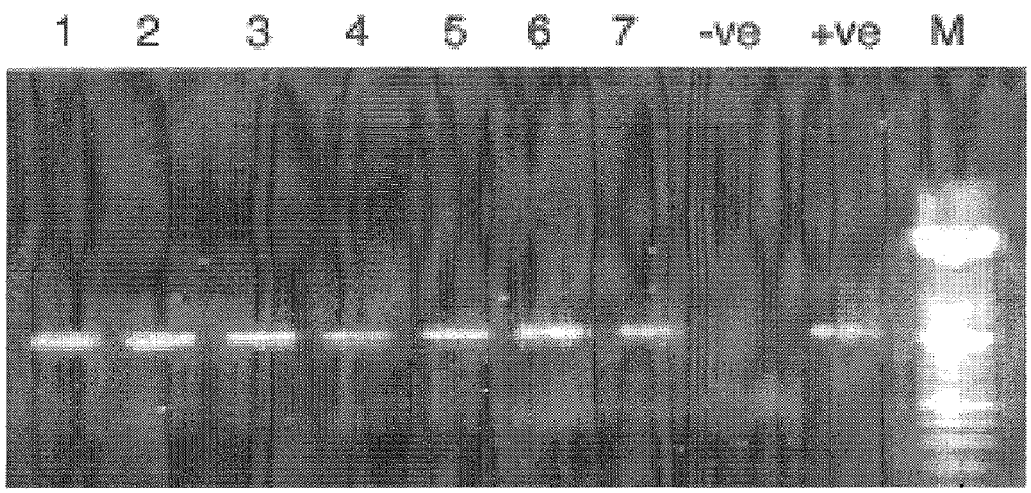
FIG. 4: Amplification of anti-COMT in the genome by PCR. Lane 1-7 denotes putative transformants; −ve denotes control plant; +ve denotes antisense construct in bacteria and M denotes the marker.

B) Restriction Analysis of Antisense Cassettes of CCoAOMT Gene for Plant Transformation The method used was same as above (FIG. 2).

Figure 5:
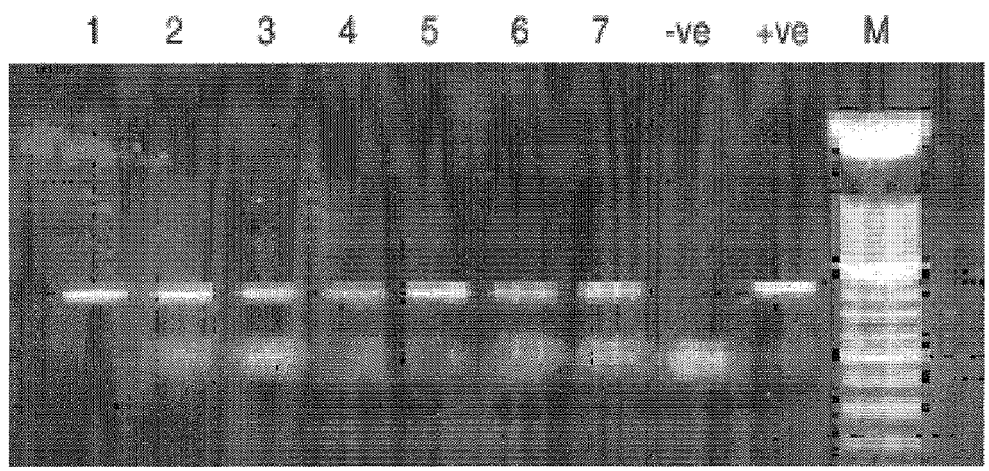
FIG. 5: Amplification of anti-CCoAOMT in the genome by PCR. Lane 1-7 denotes putative transformants; −ve denotes control plant; +ve denotes antisense construct in bacteria and M denotes the marker.

Identification of Anti-COMT in the Genome by PCR:

The total genomic DNA was used for identification of the presence of anti-COMT gene in the genome. For PCR, the forward primer was designed from the promoter at 1393 bp and the reverse primer was made from 5' region of the gene. The total amplified region is 1.2 kb (0.4 kb of the promoter region and 0.8 kb of the gene fragment used for the antisense construct) (FIG. 5).

Primer sequences used for the PCR screening of anti COMT gene in transformants:

Forward primer: 5' gaa ttc tgt ttc aaa cta cct ggt gg 3' (SEQ ID NO 3)

Reverse primer: 5' gaattc atg ggg tcg acg gcg gag gac gtg 3' (SEQ ID NO 4).

Figure 6:
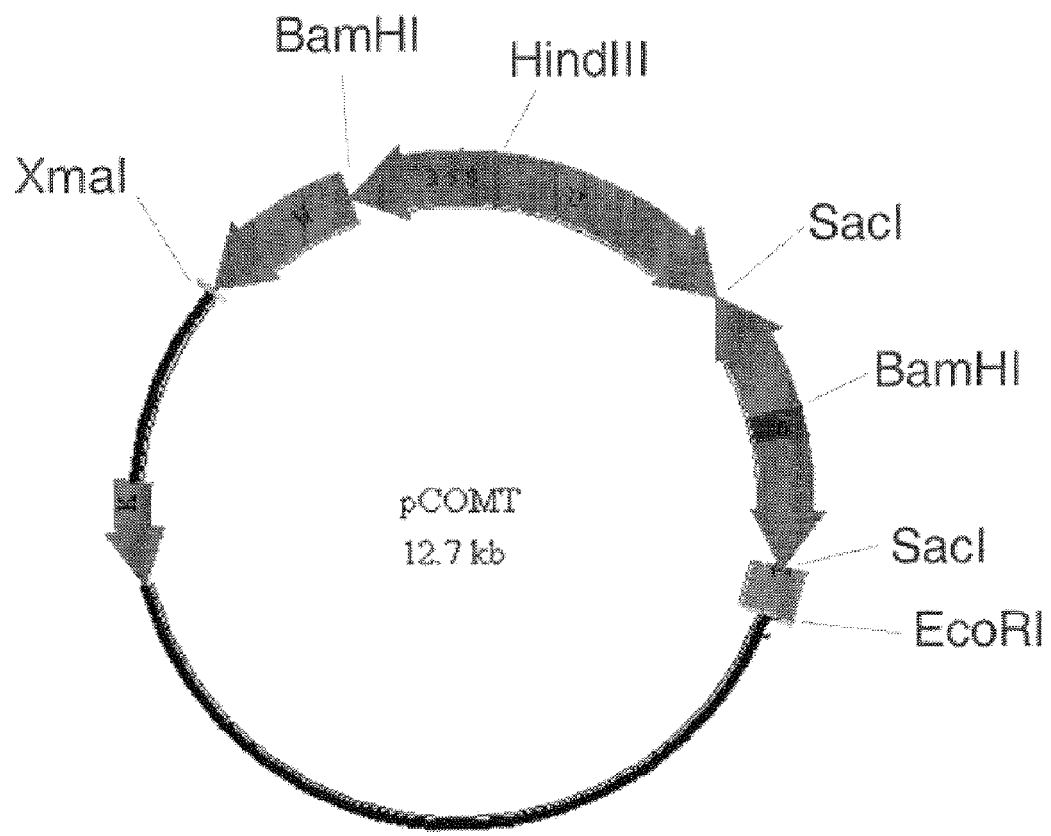
FIG. 6: Double strand mediated anti-COMT construct.
Figure 7:
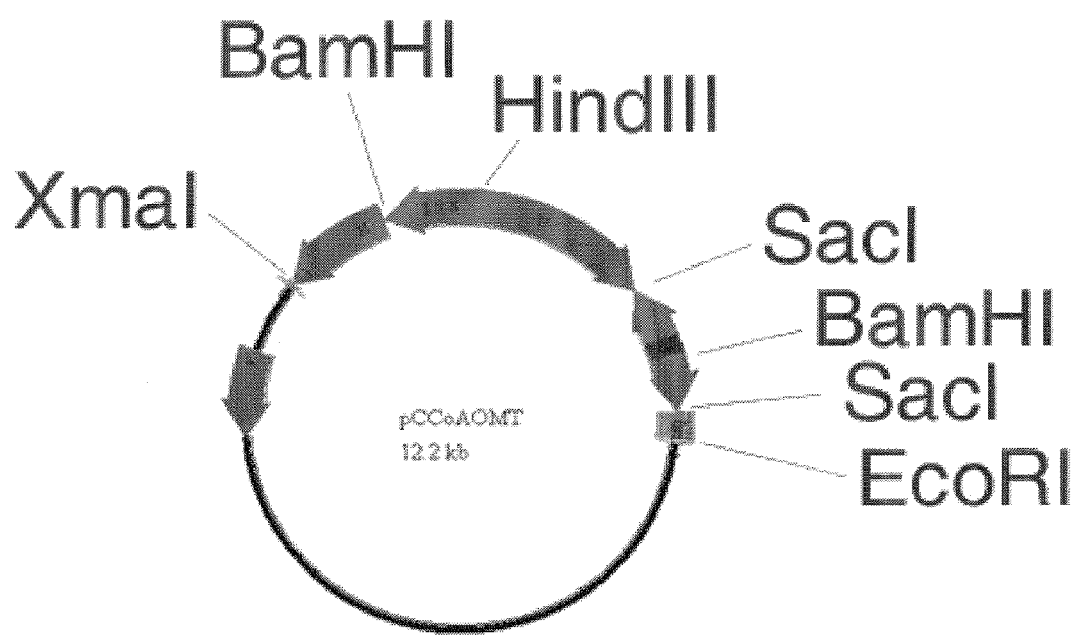
FIG. 7: Double strand mediated anti-CCoAOMT construct.
Figure 8:
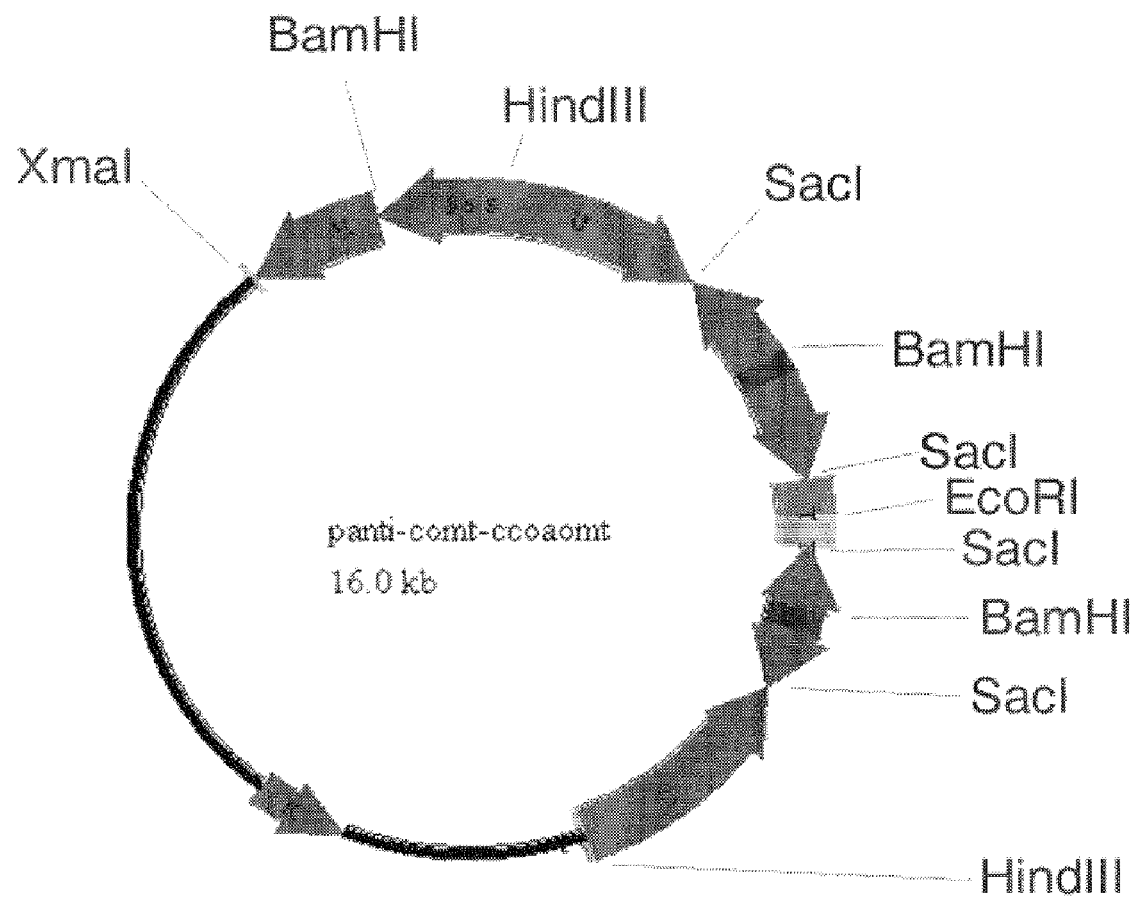
FIG. 8: Double strand mediated anti-COMT and anti-CCoAOMT construct.

Identification of Anti-CCoAOMT in the Genome by PCR:

The total genomic DNA was used for identification of the presence of anti-CCoAOMT gene in the genome. For PCR, the forward primer was designed from the promoter at 1393 bp and the reverse primer was made from 5' region of the gene. The total amplified region is 0.89 kb (about 0.4 kb of the promoter region and about 0.49 kb of the gene fragment used for the antisense construct) (FIG. 6).

Primer sequences used for PCR screening of anti CCoAOMT gene in transformants:

```
Forward primer:
                                  (SEQ ID NO 3)
5' gaa ttc tgt ttc aaa cta cct ggt gg 3'

Reverse primer:
                                  (SEQ ID NO 4)
5' gaattc atg ggg tcg acg gcg gag gac gtg 3'
```

Transformation of Sweet Sorghum (*Sorghum bicolor*) from Shoot Tip Explants:

Seeds surface sterilized with Tween 20 (5 min) and 0.2% mercuric chloride (7 min) were washed with sterile distilled water. Then seeds were incubated on sterile filter paper soaked with sterile distilled water in petriplates. After 3 days incubation in dark the shoot tips generated were excised and infected with infection medium having *Agrobacterium* suspension in it for 20 min. The explants were inoculated on co-cultivation medium and kept in dark for 3 days at 25° C. The explants were occasionally washed with cefotaxime and distilled water to prevent bacterial contamination and transferred on MS with 2 mg/l 2,4-D, 30 gm/l sucrose and 250 mg/l cefotaxime and kept in dark for 12 days for callus formation. Callus portion at the cut ends of shoot tips were excised and transferred to regeneration medium with hygromycin selection (MS with 30 g/l sucrose, 2 mg/l BAP and 2 mg/l hygromycin) and kept them in 2:1 light/dark periodic condition at 28° C. After 2 weeks, green calli were transferred on the same medium containing higher concentration of selection marker (4 mg/l hygromycin). Shoots obtained were transferred on the same medium with higher concentration of hygromycin (5 mg/l) for 2 months with periodic sub-culturing every 2 weeks. Elongated shoots were allowed to rooting medium for root generation. Full grown plantlets were finally selected on ½ MS liquid medium with 6 mg/l hygromycin. Plantlets generated from a single callus were described as single line.

The *Agrobacterium*-mediated Transformation:

The *Agrobacterium*-mediated transformation process of the invention can be broken into several steps. The basic steps include an infection step; a co-cultivation step; an optional resting step; a selection step; and a regeneration step.

In the infection step, the cells to be transformed are isolated and exposed to *Agrobacterium*. If the target cells are immature embryos, the embryos are isolated and the cells contacted with a suspension of *Agrobacterium*. As noted above, the *Agrobacterium* has been modified to contain a gene or nucleic acid of interest. The nucleic acid is inserted into the T-DNA region of the vector. General molecular techniques used in the invention are provided, for example, by Sambrook et al. (eds.) *Molecular Cloning: A Laboratory Manual*, 1989, Cold Spring Harbor Laboratory Press, Cold Spring Harbor, N.Y.

The concentration of *Agrobacterium* used in the infection step and co-cultivation step can affect the transformation frequency. Likewise, very high concentrations of *Agrobacterium* may damage the tissue to be transformed, such as the immature embryos, and result in a reduced callus response. Thus, the concentration of *Agrobacterium* useful in the methods of the invention may vary depending on the *Agrobacterium* strain utilized, the tissue being transformed, the sorghum genotype being transformed, and the like. To optimize the transformation protocol for a particular sorghum line or tissue, the tissue to be transformed, (immature embryos, for example), can be incubated with various concentrations of *Agrobacterium*. Likewise, the level of marker gene expression and the transformation efficiency can be assessed for various *Agrobacterium* concentrations. While the concentration of *Agrobacterium* may vary, generally optical density 0.7 to 1.0 at 600 nm was used in the present invention.

The tissue to be transformed is generally added to the *Agrobacterium* suspension in a liquid contact phase containing a concentration of *Agrobacterium* to optimize transformation efficiencies. The contact phase facilitates maximum contact of the cells/tissue to be transformed with the suspension of *Agrobacterium*. The cells are contacted with the suspension of *Agrobacterium* for a period of at least about three 3 minutes to about 15 minutes, preferably about 4 minutes to about 10 minutes, more preferably about 5 minutes to about 8 minutes The liquid contact phase of the infection step takes place in a liquid solution MS media along with 68.5 g/l sucrose, 36 g/l glucose, 100 µM acetosyringone and the pH adjusted to 5.2. The other media used in this invention are: Co-cultivation media (MS with 20 g/l sucrose, 10 g/l glucose, 2 mg/l 2,4-D, 100 µM acetosyringone and 8.5 g/l agar, pH 5.8), Bacterial culture media (YEP Media—Yeast extract—10 g/l, Peptone—10 g/l and Sodium Chloride—5 g/l), Infection Media (MS with 68.5 g/l sucrose, 36 g/l glucose and 100 µM acetosyringone, pH 5.2), Regeneration Media (MS with 30 g/l sucrose, 2 mg/l BAP and 8.5 g/l agar) and Rooting Media (½ MS with 20 g/l sucrose, 0.5 mg/l IAA and 0.5 mg/l NAA)

Concentration of *Agrobacterium* During Infection

O.D. of *Agrobacterium*—between 0.7-1.0

Following the co-cultivation step, or following the resting step, where it is used, the transformed cells are exposed to selective pressure to select for those cells that have received and are expressing polypeptide from the heterologous nucleic acid introduced by *Agrobacterium*. Where the cells are embryos, the embryos are transferred to plates with solid medium that includes both an antibiotic to inhibit growth of the *Agrobacterium* and a selection agent. The agent used to select for transformants will select for preferential growth of explants containing at least one selectable marker insert positioned within the super binary vector and delivered by the *Agrobacterium*.

Generally, any of the media known in the art suitable for the culture of sorghum can be used in the selection step, such as media containing N6 salts or MS salts supplemented with 30 g/l sucrose, 2 mg/l 2,4-D and kept in dark for 15 days. During selection, the embryos are cultured until callus formation is observed. Typically, calli grown on selection medium are allowed to grow to a size of about 1.5 to about 2 cm. diameter After the calli have reached the appropriate size, the calli are cultured on regeneration medium in the dark for several weeks, generally about 1 to 3 weeks to allow the somatic embryos to mature. Preferred regeneration media include media containing MS media supplemented with 30 g/l sucrose, 2 mg/l BAP and 8.5 g/l agar. The calli are then cultured on rooting medium in a light/dark cycle until shoots and roots develop Small plantlets are then transferred to tubes containing rooting medium and allowed to grow and develop more roots for approximately another week. The plants are then transplanted to soil mixture in pots in the greenhouse.

Explants Used:

Shoot apical meristem cut from the germinated seed.

Transformation Protocol of *Sorghum bicolor* from Shoot Tip Explants:

Seeds surface sterilized with Tween 20 (5 min) and 0.2% mercuric chloride (7 min) were washed with sterile distilled water. Then seeds were incubated on sterile filter paper soaked with sterile distilled water in petriplates. After 3 days incubation in dark the shoot tips generated were excised and infected with infection medium having *Agrobacterium* suspension in it for 20 min. The explants were inoculated on co-cultivation medium and kept in dark for 3 days at 25° C. The explants were occasionally washed with cefotaxime and distilled water to prevent bacterial contamination and transferred on MS with 2 mg/l 2,4-D, 30 gm/l sucrose and 250 mg/i cefotaxime and kept in dark for 12 days for callus formation. Callus portion at the cut ends of shoot tips were excised and transferred to regeneration medium with hygromycin selection (MS with 30 g/l sucrose, 2 mg/l BAP and 2 mg/l hygromycin) and kept them in 2:1 light/dark periodic condition at 28° C. After 2 weeks, green calli were transferred on the same medium containing higher concentration of selection marker (4 mg/l hygromycin). Shoots obtained were transferred on the same medium with higher concentration of hygromycin (5 mg/l) for 2 months with periodic subculturing every 2 weeks. Elongated shoots were allowed to rooting medium for root generation. Full grown plantlets were finally selected on ½ MS liquid medium with 6 mg/l hygromycin. Plantlets generated from a single callus were described as single line.

Enzymatic Assay of the Two Genes Caffeic Acid-O-Methyltransferase (COMT) And CaffeoylCoA-O-Methyltransferase (CCoAOMT) at Least from the Callus of the Transformed Cells Methods: Control and transformed calli were collected and homogenized in liquid nitrogen. Powdered tissue was extracted at 4° C. in extraction buffer (100 mM Tris-HCl, pH 7.5, 10% glycerol, 2 mM DTT, 0.2 mM $MgCl_2$, 1 mM phenylmethylsulfonyl fluoride) for 1 hr and desalted on G-50 columns. Protein concentrations were determined using Bradford methods with BSA as standard. The assay mixtures contained 5 µl of $[^{14}CH_3]$-S-adenosyl-L-Met, 5 µl of caffeic acid (1 mM) or caffeoyl CoA (1 mM), 30 µl of assay buffer (100 mM Tris-HC1, pH 7.5, 10% glycerol, 2 mM DTT, 0.2 mM $MgCl_2$), and 5 µl of protein extract, were incubated at 30° C. for 30 min. The reactions were stopped by adding 50 µl of 0.2 M HC1 and 10 µl of 3 M NaOH in case of COMT and CCoAOMT respectively. After keeping the mixture at 37° C. for 10 min, the mixture for CCoAOMT was acidified with 40 µl of 1M HCl. Labeled ferulic acid was extracted with 200 µl of hexane:ethyl:acetate (1:1, v/v). The separated organic phase was transferred to scintillation vials and the radioactivity was measured.

Results: Enzymatic activity in five transformed calli in each transformed lines was measured to verify the accountability of the antisense strategy as a preliminary study. The results revealed that some of the calli were responding significantly (indicated by asterix) though in most cases alteration of the activity was found insignificant. However, the results have confirmed that the strategy adopted for down regulating the expression level has been effective.

| Calli | Activity of COMT (pmol/sec/ mg of total protein) | Activity of CCoAOMT (pmol/sec/ mg of total protein) |
|---|---|---|
| A. Control (Untransformed lines) | | |
| 1. | 3.12 | 7.23 |
| 2. | 4.23 | 7.45 |
| 3. | 3.92 | 6.89 |
| B. $p^{anti-comt}$ transformed lines | | |
| 1. COMT1 | 2.89 | — |
| 2. COMT4 | 3.01 | — |
| 3. COMT5 | 3.89 | — |
| 4. COMT6 | 2.25* | — |
| 5. COMT9 | 4.32 | — |
| C. $p^{anti-ccoaomt}$ transformed lines | | |
| 1. CCoAOMT1 | — | 5.52* |
| 2. CCoAOMT2 | — | 7.39 |
| 3. CCoAOMT4 | — | 8.01 |
| 4. CCoAOMT5 | — | 6.99 |
| D. CCoAOMT6 | — | 6.59 |

Estimation of G and S Lignin:

Method: Lignin composition of transformed and untransformed plants was determined under the condition of thioacidolysis and the Raney nickel desulfurization method of Lapierre et al. (1986). Thioacidolysis was performed using ~20 mg of cell wall residue reacted with 15 ml of 0.2 M boron trifluoride and etherate in an 8.75:1 dioxane/ethanethiol mixture. An aliquot of the thioacidolysis solution in methylene chloride was mixed with 1 ml Raney nickel aqueous slurry for desulfurization. The composition of lignin-derived monomers was determined by gas chromatography-mass spectrometry as their trimethylsilyl derivatives.

Result:

| Sample | G (µmol/g dry wt) | S (µmol/g dry wt) |
|---|---|---|
| A. Control (Untransformed lines) | | |
| 1. Control 1 | 440 | 375 |
| 2. Control 2 | 395 | 400 |
| 3. Control 3 | 410 | 396 |
| B. $p^{anti-comt}$ transformed lines | | |
| 1. COMT1 | 440 | 360 |
| 2. COMT2 | 390 | 415 |
| 3. COMT3 | 381 | 262 |
| 4. COMT6 | 460 | 400 |

-continued

| Sample | G (μmol/g dry wt) | S (μmol/g dry wt) |
|---|---|---|
| C. p$^{anti-ccoaomt}$ transformed lines | | |
| 1. CCoAOMT 1 | 315 | 365 |
| 2. CCoAOMT 2 | 421 | 405 |
| 3. CCoAOMT5 | 375 | 452 |
| D. p$^{anti-comt-ccoaomt}$ transformed lines | | |
| 1. COMT-CCoAOMT 1 | 307 | 312 |
| 2. COMT-CCoAOMT 3 | 375 | 397 |

Composition of G and S Lignin Content in Sweet Sorghum

The average content for G and S lignin in stem of 20 days old wild sweet sorghum plant was found to be 415 μmol/g dry samples and 390 μmol/g dry samples respectively. The average syringyl/guaiacyl lignin ratio (S/G ratio) is ~0.94. Reduction of total lignin was observed in transformed line COMT. However, increment of S/G ratio was observed to 1.2 in case of transformed line CCoAOMT in spite of the reduction in S/G ratio to 0.7 was observed in case of transformed line COMT. The result indicated that double strand antisense mediated down regulation of CCoAOMT was suitable for generation of sweet sorghum plants with altered lignin content and composition.

Media Compositions Involved in Present Invention:

Co-Cultivation Media:
  MS+20 g/l sucrose+10 g/l glucose+2 mg/l 2,4-D+100 μM acetosyringone+8.5 g/l agar, pH 5.8

Bacterial Culture Media:
  YEP Media—gm per liter
  Yeast extract—10 g
  Peptone—10 g
  Sodium Chloride—5 g Infection Media:
  MS with 68.5 g/l sucrose, 36 g/l glucose and 100 μM acetosyringone, pH 5.2

Regeneration Media:
  MS with 30 g/l sucrose, 2 mg/l BAP and 8.5 g/l agar

Rooting Media:
  ½ MS with 20 g/i sucrose, 0.5 mg/l IAA and 0.5 mg/l NAA

Concentration of *Agrobacterium* During Infection
  O.D. of *Agrobacterium*—between 0.7-1.0

Conditions for Callus Induction:
  Callus are grown in MS with 30 g/l sucrose, 2 mg/l 2,4-D media and kept it in dark for 15 days.

We claim:

1. An isolated DNA sequence isolated from sweet sorghum (*Sorghum bicolor*) encoding Caffeoyl-CoA-O-methyltransferase (CCoAOMT), the sequence comprising SEQ ID NO 2.

2. The isolated DNA sequence of claim 1, wherein the DNA is cDNA.

3. A construct comprising an isolated nucleic acid sequence comprising SEQ ID NO 2, said nucleic acid being operably associated with a promoter, wherein the first nucleic acid is in the antisense orientation and is "antisense" to at least a portion of a CCoAOMT gene, and said construct optionally comprises a second nucleic acid represented by SEQ ID NO 1 that is an antisense to nucleotide sequence that encodes caffeic acid-O-methyltransferase (COMT).

4. A host cell comprising the construct of claim 3.

5. The host cell of claim 4, wherein the host cell is *Agrobacterium tumeficiens*.

6. The construct of claim 3, wherein expression of said construct in a plant cell results in alteration of lignin content and composition in plant.

7. The construct of claim 3, wherein the first exogenous nucleic acid comprises an antisense nucleotide sequence that is antisense to at least a portion of a CCoAOMT gene.

8. The construct of claim 7, wherein the first exogenous nucleic acid comprises a nucleotide sequence that is complementary to a nucleotide sequence of at least a portion of an endogenous CCaAOMT RNA.

9. The construct of claim 8, wherein the endogenous RNA is a precursor RNA or an mRNA.

10. The construct of claim 6, wherein the second exogenous nucleic acid comprises a nucleotide sequence that is complementary to a nucleotide sequence of at least a portion of an endogenous COMT RNA.

11. A process for producing a transgenic sweet sorghum (*Sorghum bicolor*) plant having altered lignin content and composition, said process comprising:
   a. transfecting a sweet sorghum plant cell with a first isolated nucleic acid sequence comprising SEQ ID NO 2, and optionally a second isolated nucleic acid comprising SEQ ID NO 1, said nucleic acids associated with altered activity of a caffeoyl-CoA-O-methyltransferase (CCoAOMT) and caffeic acid-O-methyltranferase (COMT) in genetically engineered plants as compared to the activity of CCoAOMT and COMT in the wild plant, to yield a genetically engineered plant cell construct; and
   b. growing the plant cell into the transgenic sweet sorghum plant having altered lignin content as compared to the wild type plant.

12. The process of claim 11, wherein transfection of the plant cell is carried out with a vector comprising a first isolated nucleic acid comprising a first nucleotide sequence that is antisense to a CCoAOMT gene and optionally a second isolated nucleic acid sequence that is antisense to COMT.

13. The process of claim 11, wherein expression of the first isolated nucleic acid causes the transgenic plant cell to produce a first antisense RNA transcript having a nucleotide sequence that is complementary to a nucleotide sequence of at least a portion of an endogenous CCoAOMT RNA.

14. The process of claim 11, wherein the second isolated nucleic acid sequence is associated with reduced COMT activity.

15. The process of claim 11, wherein the altered lignin content and composition of the genetically engineered plant is characterized by an increased syringyl lignin/guaiacyl lignin ratio when compared to the syringyl/guaiacyl lignin ratio of the wild plant.

16. The process of claim 15, wherein the syringyl/guaiacyl lignin ratio is 1:2.

17. A vector comprising the construct of claim 3.

18. The vector of claim 17, wherein the vector comprises a pUC18 vector.

19. The process of claim 13, wherein the endogenous RNA is a precursor RNA or an mRNA.

* * * * *

SEQUENCE LISTING

<160> NUMBER OF SEQ ID NOS: 4

<210> SEQ ID NO 1
<211> LENGTH: 1089
<212> TYPE: DNA
<213> ORGANISM: ARTIFICIAL
<220> FEATURE:
<223> OTHER INFORMATION: cDNA Sequence of caffeic acid O-methyl
      transferase (COMT)

<400> SEQUENCE: 1

```
atggggtcga cggcggagga cgtggcggcg gtggcggacg aggaggcgtg catgtacgcg      60
atgcagctgg cgtcgtcgtc gatcctcccc atgacgctga agaacgcgct ggagctgggc     120
ctgctggagg tgcttcagaa ggacgccggc aaggcgctgg cggcggagga ggtggtggcg     180
cggctgcccg tggcgccgac gaaccccgcc gcggcggaca tggtggaccg catgctccgc     240
ctcctcgcct cctacgacgt cgtgaggtgc cagatggagg acaaggacgg caagtacgag     300
cgtcggtact ccgccgcccc cgtcggcaag tggctcaccc taacgaggac ggcgtctcc     360 atggccgccc tcgcgctcat gaaccaggac aaggtcctca tggagagctg gtactacctc     420
aaggacgcgg tgcttgacgg cggcatcccg ttcaacaagg cgtacgggat gacggcgttc     480
gagtaccacg gcacggaccc gcgcttcaac cgcgtgttca acgagggcat gaagaaccac     540
agcgtgatca tcaccaagaa gctcctcgag ttctacacgg gcttcgacga gtccgtctcg     600 acgctctcg acgtgggcgg cggcatcggc gccaccttac acgccatcac ctcccaccac     660
tcccacatca ggggatcaa cttcgacctc ccgcacgtga tctccgaggc gccgccgttc     720
cccggcgtgc agcacgtcgg cggggacatg ttcaagtcgg tgccggccgg cgacgccatc     780
ctcatgaagt ggatcctcca cgactggagc gacgcgcact cgccacgct gctcaagaac     840 tgctacgacg cgctgccgga aagggcggc aaggtgatcg tcgtcgagtg cgtgctgccg     900
gtgaccaccg acgccgtccc caaggcgcag ggcgtgttcc atgtcgacat gatcatgctc     960
gcgcataacc ccggcggcag ggagcggtac gagcgggagt tccgtgacct cgccaaggcc    1020
```

```
gctggcttct ctgggttcaa ggccacctac atctacgcca acgcctgggc catcgagttc    1080
atcaagtaa                                                             1089

<210> SEQ ID NO 2
<211> LENGTH: 759
<212> TYPE: DNA
<213> ORGANISM: ARTIFICIAL
<220> FEATURE:
<223> OTHER INFORMATION: cDNA of CaffeoylCoA-O-methyltransferae CCoAOMT
      isolated from sweet sorghum (Sorghum bicolor)

<400> SEQUENCE: 2
atggccgaaa acggcgaaga gcagcaggcg aacggcaacg gcgagcagaa gacccggcat      60
caggaagtag ggcacaagag cctgctcaag agcgacgagc tctaccagta catcctggac     120
acgagcgtgt acccgcggga gccggagagc atgaaggagc tccgcgagat caccgccaag     180
cacccatgga acctgatgac gacctccgcc gacgaggggc agttcctcaa catgctcatc     240
aagctcatcg gcgccaagaa gaccatggag atcgcgtct cacaccggcta ctccctcctt     300 gctactgcca tggctcttcc cgatgatggc aagattctag ctatggatat taaccgggaa     360
aactacgaga ttggtcttcc agtgattgaa aaggctggac tggcccacaa gatcgacttc     420
cgcgagggcc ccgcgctccc cgtcctcgac gacctcatcg ccgacgagaa gaaccacggg     480
tcgttcgact tcgtcttcgt ggacgccgac aaggacaact acctcaacta ccacgaccgg     540
ctgctcaagc tggtgaagct gggggcctc atcggctatg acaacacact gtggaacggg     600
agcgtcgtgc tgcccgacga cgccccgatg cggaagtaca ttcgcttcta ccgcgatttc     660
gtcctcgtcc tgaacaaggc gctcgcggcg gatgatcgcg tcgagatctg ccagctcccc     720
gtcggtgacg tgtgacgct gtgccggcgc gtcaagtga                             759

<210> SEQ ID NO 3
<211> LENGTH: 26
<212> TYPE: DNA
<213> ORGANISM: Artificial
<220> FEATURE:
<223> OTHER INFORMATION: Forward primer for amplification of CCoAOMT

<400> SEQUENCE: 3
gaattctgtt tcaaactacc tggtgg                                           26

<210> SEQ ID NO 4
<211> LENGTH: 30
<212> TYPE: DNA
<213> ORGANISM: Artificial
<220> FEATURE:
<223> OTHER INFORMATION: Reverse primer for amplification of CCoAOMT

<400> SEQUENCE: 4
gaattcatgg ggtcgacggc ggaggacgtg                                       30
```